(12) United States Patent
Friedman

(10) Patent No.: US 7,015,423 B2
(45) Date of Patent: Mar. 21, 2006

(54) HEATING DEVICE FOR DENTAL MATERIAL

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 381 days.

(21) Appl. No.: 10/440,884

(22) Filed: May 19, 2003

(65) Prior Publication Data

US 2004/0234921 A1    Nov. 25, 2004

(51) Int. Cl.
  *A61C 5/04*   (2006.01)
  *A61C 19/00*  (2006.01)
  *H05B 3/00*   (2006.01)

(52) U.S. Cl. ............ 219/385; 219/386; 219/433; 219/201; 222/146.5; 433/32

(58) Field of Classification Search ............ None
See application file for complete search history.

(56) References Cited

U.S. PATENT DOCUMENTS

| | | | | | |
|---|---|---|---|---|---|
| 1,792,434 | A | * | 2/1931 | Lockwood | 219/385 |
| 1,805,291 | A | * | 5/1931 | Monnot | 219/473 |
| 3,228,566 | A | * | 1/1966 | Knox, Jr. | 222/146.5 |
| 3,430,816 | A | * | 3/1969 | Nadhemy et al. | 222/146.5 |
| 3,466,752 | A | * | 9/1969 | Braun | 433/32 |
| 3,902,043 | A | * | 8/1975 | Rogan | 219/242 |
| 4,287,408 | A | * | 9/1981 | Wilson | 219/475 |
| 5,549,543 | A | * | 8/1996 | Kim | 600/169 |
| 5,984,302 | A | * | 11/1999 | Garrone | 271/227 |
| 6,204,485 | B1 | * | 3/2001 | Williams | 219/249 |
| 6,236,020 | B1 | * | 5/2001 | Friedman | 219/385 |
| 6,320,162 | B1 | * | 11/2001 | Friedman | 219/385 |
| 6,444,956 | B1 | * | 9/2002 | Witcher et al. | 219/429 |
| 6,459,073 | B1 | * | 10/2002 | Berger | 219/433 |
| 2002/0064753 | A1 | * | 5/2002 | Philp | 433/32 |

* cited by examiner

Primary Examiner—Joseph Pelham

(57) ABSTRACT

A heating device into which a compule of dental material can be inserted to elevate the temperature of the dental material to above ambient temperature prior to clinical use having a base for housing a heating element, a temperature control mechanism for controlling the temperature of the heating element, a power connection for electrically connecting the temperature control mechanism to a source of power and a heating receptacle removably mounted on the base. The heating receptacle comprises a heating tray composed of a conductive material and an upstanding section extending from the heating tray and having a heating chamber open to the atmosphere which is adapted to receive one end of a conventional dispenser in which the compule of dental material is stored for raising the temperature of said dental material in said compule to an elevated temperature.

9 Claims, 2 Drawing Sheets

HEATING DEVICE FOR DENTAL MATERIAL

FIELD OF THE INVENTION

This invention relates to a heating device for heating the end of a standard dispenser in which a compule, ampule or other dose packaging configuration of a dental material is stored and more particularly to a heating device into which a conventional dispenser containing dental material can be inserted to elevate the temperature of the dental material to above ambient temperature prior to clinical use.

BACKGROUND OF INVENTION

The properties of many dental materials are enhanced when preheated just prior to clinical usage. Examples of such dental materials include etching agents, bleaching compositions, dental cements, impression materials and more particularly photocurable dental restorative materials. It is typical to prepackage a unit dosage of the dental material in a cartridge, which shall hereafter be referred to as a compule. A dispensing syringe or gun is commonly used in the dental profession to discharge the contents of dental material from a compule directly into the patient's mouth during clinical usage.

Applicant teaches in U.S. Pat. Nos. 6,236,020 and 6,320,162, each disclosure of which is herein incorporated by reference, a method and apparatus by which a compule of dental material can be heated prior to insertion into a dispensing syringe or gun. However, in the preparation of a dental restoration a compule may be dispensed several times in sequence so as to form successive layers. In fact, the American Dental Association and all manufacturers of dental light cured materials recommend using a layering technique involving curing of filling material in successive 2 mm maximum layers as the best way to achieve the most polymerization and hence the best physical properties. When a layering technique is used, removing the compule from the standard dispenser to reheat it before placing it back into the dispenser is cumbersome and time consuming. This procedure may, in fact, have to be repeated three or four times during the course of any given restoration so that each layer is preheated to a uniform temperature and is accordingly a drawback in the use of the method and apparatus of the aforementioned patents.

A dispensing syringe or gun which incorporates a heating assembly within the dispenser itself is taught by Applicant in U.S. Pat. No. 6,312,254. Although this arrangement will overcome the disadvantages of removing and reinserting the compule in the dispenser each time the compule is partially dispensed this is a substantially more complex and expensive dispensing syringe than the standard dispenser, which is in common usage.

The present invention permits a conventional dispenser with any known prepackaged compule of dental material to be heated without removal from the dispenser.

SUMMARY OF THE INVENTION

The heating device of the present invention is adapted to receive the end of a standard dispenser in which a compule of dental material is removably stored for heating the compule without requiring its removal from the dispenser. As such, any standard dispenser may be used which has an elongated end, preferably of tubular geometry, in which a compule of dental material is removably stored. The heating device of the present invention is also capable of storing unpackaged dental material in any consistency and shielding the loosely stored dental material from exposure to room or operatory light so that polymerization is not initiated prematurely.

The heating device of the present invention comprises a base for housing a temperature control mechanism, a heating element electrically connected to the temperature control mechanism, a power connection for electrically connecting the temperature control mechanism to a source of power and a heating receptacle removably mounted on the base with the heating receptacle comprising a heating tray composed of a thermally conductive material, an upstanding section extending from the heating tray having a heating chamber adapted to receive the end of a standard dispenser in which a compule of dental material is stored for heating said compule to an elevated temperature. In the preferred configuration guide means surrounds the upstanding section to further extend said upstanding section for guiding the end of the standard dispenser into the heating chamber.

BRIEF DESCRIPTION OF THE DRAWINGS

Other features and advantages of the present invention will become apparent from the following detailed description of the invention when read in conjunction with the accompanying drawings of which.

DETAILED DESCRIPTION OF THE PREFERRED EMBODIMENT

Figure 1:
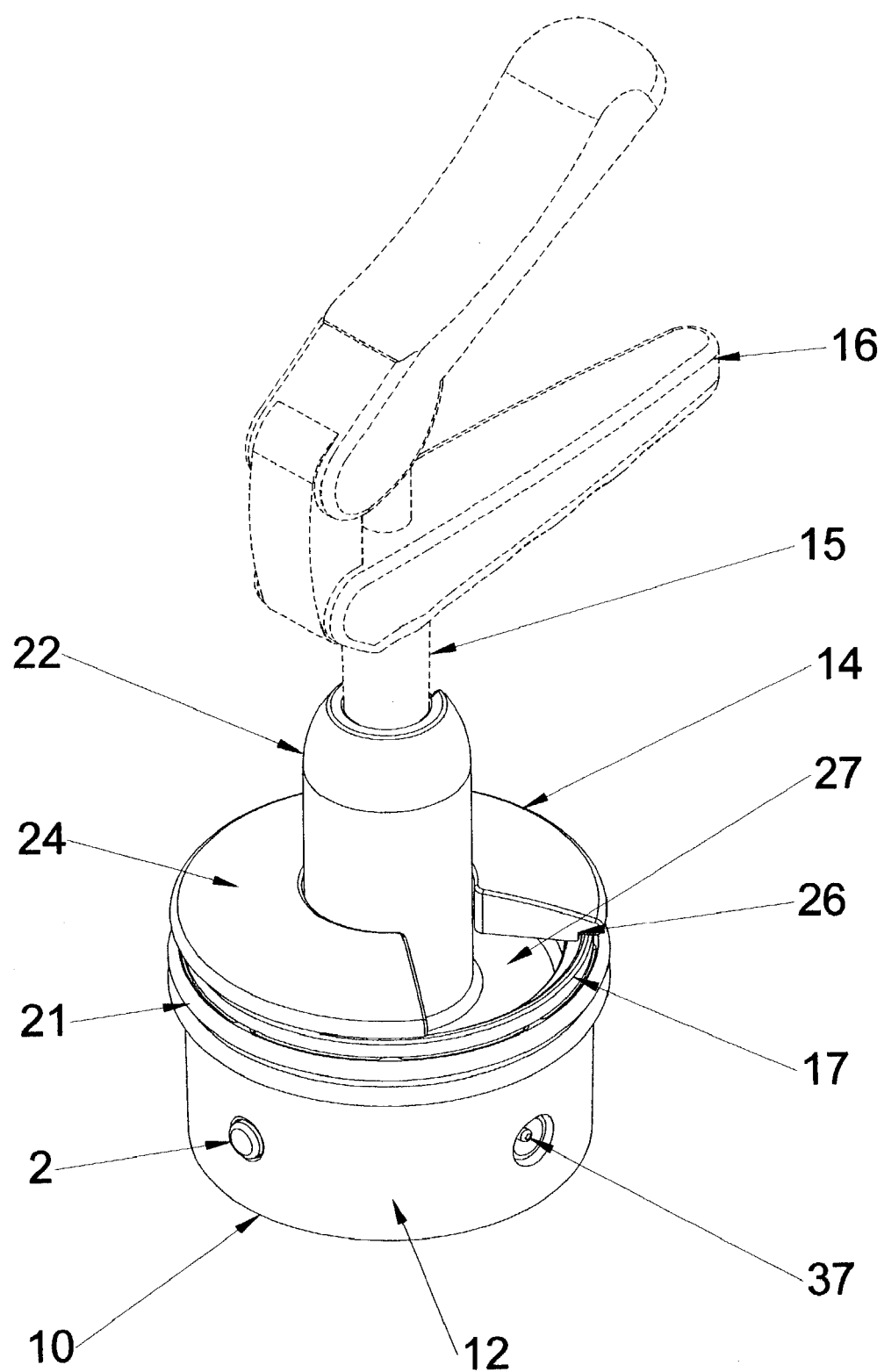
FIG. 1 is a perspective view of the heating device of the present invention shown supporting a standard dispenser for heating a compule of dental material located at the end of the dispenser inserted into the heating device.
Figure 3:
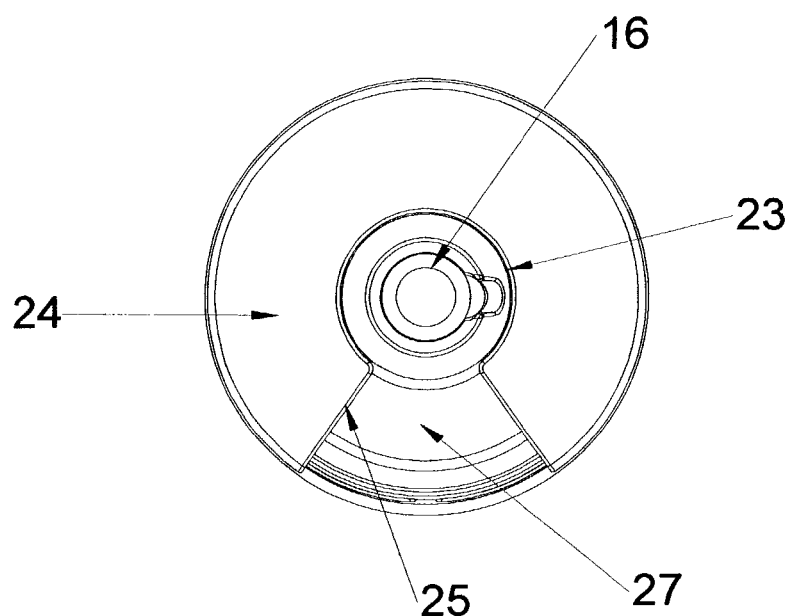
FIG. 3 is a top view of the heating device of FIG. 2 with the dispenser syringe removed.
Figure 2:
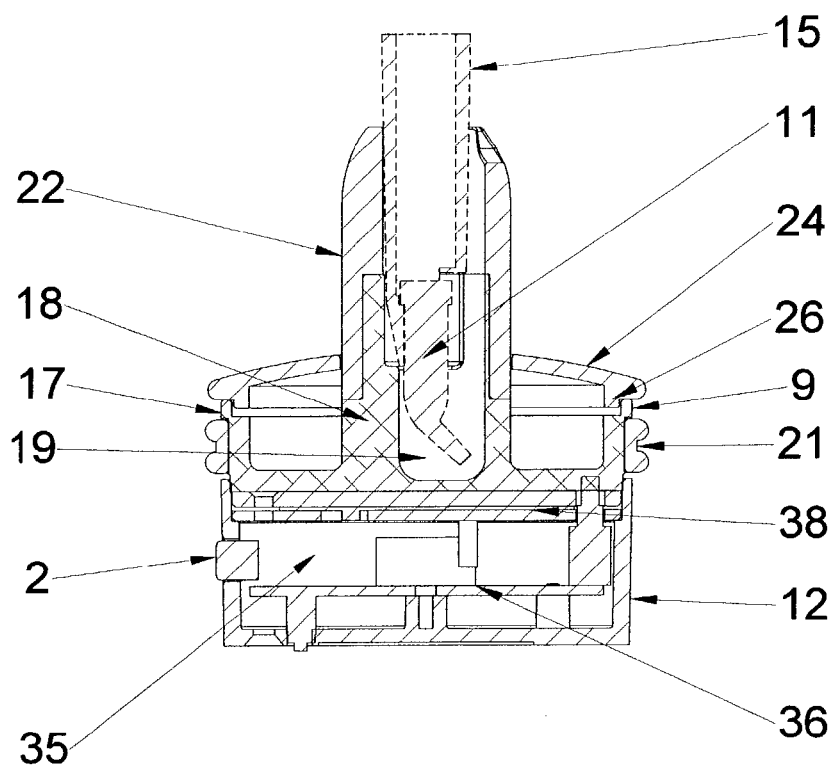
FIG. 2 is a cross sectional view of the heating device of the present invention taken along the lines 2—2 of FIG. 1.

The heating device of the present invention is shown represented by the reference number 10 in FIGS. 1–3 and comprises, in combination, a base 12 and a removable heating receptacle assembly 14 adapted to receive the end 15 of a standard dispensing gun 16 in which a dental compule is placed. The heating receptacle assembly 14 includes a heating tray 17 and a hollow upstanding section 18, which extends upwardly from the heating tray 17. The hollow upstanding section 18 forms a heating chamber 19 internal of the upstanding section 18.

The heating tray 17 and the upstanding section 18 are both composed of thermally conductive metal and may be machined or molded as a single unit. Metals such as aluminum, copper and various bronze or brass alloys make good thermal conductors and have thermal conductivity in the range of 65 to 225 BTU per square foot per hour per degree F. at 68° F. To protect the surface of the metal various commercially coatings are available. Certain synergistic Teflon coatings commercially available as Magnaplate™, Tufram™, Xylan™ and Tiodize™, provide a non-stick surface that prevents composite filling material from adhering to its surface and allows the part to be chemically disinfected or autoclaved.

The heating tray 17 is in the form of a flat plate like member, which is adapted to be removably mounted on the base 12. A thermally insulating plastic ring 21 surrounds the heating tray 17 to permit its safe and comfortable removal from the base 12 in a heated condition. A plastic sleeve 22 surrounds the upstanding section 18 and further extends it upwardly for guiding the tubular end 15 of the standard dispensing gun 16 into the heating chamber 19. The plastic sleeve 22 is removably attached to the upstanding section 18 of the heating tray 17 and its shape may be modified to accommodate the end shape and diameter of a variety of different dispensing guns or syringes in which the dental compule is stored.

A plastic cover 24 having a pie shaped opening 25 and an annular ledge 26 is mounted on the heating tray 17 with the ledge 26 separating the cover 24 from the tray 17 to form an open area 27 on the upper surface of the tray 17 into which loose dental filling material (not shown) may be extruded. This allows the unpackaged dental filling material on the tray 17 to be heated directly. The cover 24 is manually rotatable to shield the filling material from light. The plastic cover 24 also serves to insulate the heated material from surrounding air and maintain the material at an elevated temperature.

The base 12, which is functionally similar to the base member in U.S. Pat. No. 6,236,020, has a cavity 35 in which is mounted a temperature control mechanism 36, a power connection 37 and a heating element 38. The heating element 38 is an electrical resistive heater for heating the tray 17 to a controlled temperature and is preferably in the form of a filamentary wire or flat conductor of graphite, tungsten, copper or other suitable conductive material wound in a serpentine or other geometrical arrangement to form a series electrical path with the temperature control mechanism 36. The heating element 38 is embedded in a plastic, ceramic or rubber compound and is adhered to a flat metal plate 39 so as to form a flat surface upon which the heating tray 17 rests.

The temperature control mechanism 36 controls the temperature of the heating element 38 and may consist of a thermostat or another temperature control device such as a thermistor or a temperature control circuit consisting of a thermistor or thermocouple attached to the plate 39 and including a microprocessor or other type feedback control (not shown). It should be understood that any conventional type of temperature control mechanism 36 may be used for this purpose and is preferably preadjusted to bring the temperature of the heating element 38 to a suitable elevated temperature above ambient room temperature but preferably between 100° F. and 180° F. The optimum temperature setting of the heating element 38 is 130° F. to 140° F. for photocurable dental materials.

The power connection 37 extends through the base 12 to an external connection (not shown) for electrically connecting the temperature control mechanism 36 to a suitable external source of electrical power (not shown). Although not shown the heating device 10 may also be operated from a rechargeable battery. The temperature control mechanism 36 may also be used to provide a visual indication through a suitable visible light source (not shown) that the thermostat or temperature control mechanism 36 is operational and the heating device has reached operating temperature. A power switch 2 turns the heating device on and off.

As shown in FIG. 2 the heating tray 17 sits on top of the base 12 and can be removed and brought to a location close to the point of application, such as the dentists bracket tray. The thermal conductivity and mass of the tray material act as a heat sink and provide for 2–5 minutes of use at elevated temperature when used in this manner.

In operation the end 15 of a standard dispensing syringe 16 would be inserted through the slot 23 in the plastic guide sleeve 22 which will align the dispensing syringe 16 with the dental composite compule 11 stored at the end 15 inside the heating so with the end 15 of the syringe 16 in the heating chamber 19. In this way the heating chamber 19 heats the end 15 of the syringe 16 and, in turn, the dental composite material in the compule 11 is radiantly heated to a desired elevated temperature. Any loose filling material stored on the heating tray 17 will also be heated to the same elevated temperature.

What is claimed is:

1. A heating device into which a conventional dispenser having a compule or ampule containing dental material can be inserted to elevate the temperature of the compule or ampule of dental material to above ambient temperature prior to dispensing the dental material from the compule or ampule for clinical use; said heating device comprising a base for housing a thermostat, a heating element electrically connected to the thermostat, a power connection for electrically connecting the thermostat to a source of power and a heating receptacle assembly removably mounted on the base, with said heating receptacle assembly comprising a heating tray composed of a conductive material and an upstanding section having a heating chamber therein extending from the heating tray for forming a heating vessel having cross sectional dimensions substantially conforming to the cross sectional dimensions of one end of said dispenser at which said a compule or ampule of dental material is located so as to raise the temperature of said compule or ampule to an elevated temperature and wherein said heating receptacle assembly is of sufficient mass to maintain the temperature of the dispenser at an elevated temperature for a reasonable time period after said assembly is removed from the base for dispensing dental material at an elevated temperature from said dispenser at a location distant from the location of the heating device.

2. A heating device as defined in claim 1 wherein said compule or ampule is removably located at one end in said dispenser.

3. A heating device as defined in claim 2 wherein said heating receptacle further comprises hollow guide means surrounding the upstanding section and being open to the atmosphere so as to further extend said upstanding section upwardly for guiding said end of the conventional dispenser storing the compule of dental material into the heating chamber.

4. A heating device as defined in claim 3 wherein said heating receptacle further comprises a removable plastic cover having an opening and an annular ledge extending from its periphery which is adapted to be mounted on the heating tray so that the ledge separates the cover from the tray to permit dental filling material to be extruded onto the upper surface of the tray with the cover being rotatable to protect the dental filling material from exposure to light and premature polymerization.

5. A heating device as defined in claim 3 wherein said heating element is mounted adjacent said heating tray and is in the form of a filamentary wire or flat conductor for forming an electrical resistive heater.

6. A heating device as defined in claim 5 wherein said temperature control mechanism for controlling the temperature of the heating element is selected from the class consisting of a thermostat or another thermal sensor and temperature control circuit.

7. A heating device as defined in claim 3 wherein said heating receptacle further comprises insulating means surrounding said heating tray to permit manually moving the tray at an elevated temperature.

8. A heating device as defined in claim 7 wherein the heating tray and upstanding section is a single unit composed of a conductive material selected from the class consisting of aluminum, copper, bronze and/or brass alloys.

9. A heating device as defined in claim 8 wherein the heating synergistic non-stick coating that prevents composite filling material from adhering to its surface and allows the part to be chemically disinfected or autoclaved.

\* \* \* \* \*